United States Patent
Mc Manus et al.

(10) Patent No.: US 7,087,560 B2
(45) Date of Patent: Aug. 8, 2006

(54) PERSONAL CARE COMPOSITION WITH SALTS OF DIHYDROXYPROPYLTRI($C_1$-$C_3$ ALKYL) AMMONIUM MONOSUBSTITUTED POLYOLS

(75) Inventors: Richard Loren Mc Manus, Shelton, CT (US); Michael Charles Cheney, Trumbull, CT (US); Alessandro Luigi Spadini, Stamford, CT (US); Bijan Harichian, Warren, NJ (US); Philip Edward Miner, Newton, CT (US)

(73) Assignee: Unilever Home & Personal Care USA, a division of Conopco, Inc., Greenwich, CT (US)

(*) Notice: Subject to any disclaimer, the term of this patent is extended or adjusted under 35 U.S.C. 154(b) by 0 days.

(21) Appl. No.: 10/973,023

(22) Filed: Oct. 25, 2004

(65) Prior Publication Data

US 2006/0089290 A1    Apr. 27, 2006

(51) Int. Cl.
*C11D 1/62* (2006.01)
(52) U.S. Cl. .................. 510/119; 510/123; 510/504
(58) Field of Classification Search ........... 510/119, 510/123, 504
See application file for complete search history.

(56) References Cited

U.S. PATENT DOCUMENTS

| | | | |
|---|---|---|---|
| 4,663,159 A | 5/1987 | Brode, II et al. | |
| 4,689,217 A | 8/1987 | Restaino et al. | |
| 4,690,817 A | 9/1987 | Davis et al. | |
| 4,775,715 A | 10/1988 | Beresniewicz et al. | |
| 5,698,183 A | 12/1997 | Langer et al. | |
| 5,773,595 A * | 6/1998 | Weuthen et al. | 536/17.9 |
| 6,290,978 B1 | 9/2001 | Mak et al. | |
| 6,432,907 B1 * | 8/2002 | Skold et al. | 510/470 |
| 6,620,410 B1 * | 9/2003 | Cho et al. | 424/70.9 |
| 6,649,177 B1 | 11/2003 | Howard et al. | |
| 6,740,317 B1 * | 5/2004 | Cho et al. | 424/70.1 |
| 6,869,977 B1 | 3/2005 | O'Lenick, Jr. et al. | |
| 2003/0206933 A1 | 11/2003 | Schulza zur Wiesche et al. | |
| 2003/0211952 A1 | 11/2003 | Erazo-Majewicz et al. | |
| 2004/0156877 A1 | 8/2004 | Tokuyama et al. | |

FOREIGN PATENT DOCUMENTS

| | | |
|---|---|---|
| EP | 1 179 339 | 2/2002 |
| EP | 1 366 742 | 12/2003 |
| JP | 63068514 | 3/1988 |
| JP | 1249709 | 10/1989 |
| JP | 9012589 | * 1/1997 |
| WO | 00/61066 | 10/2000 |

OTHER PUBLICATIONS

Dow—Quat 188 Cationic Monomer: Overview, Jun. 30, 2004.
Arch Personal Care Products Brochure—Honeyquat 50 Substantive Honey Derivative, Jan. 2004.
Arch Personal Care Products—In vivo study of moisturizing effects of HoneyQuat 50, Jan. 2004.

* cited by examiner

*Primary Examiner*—Charles Boyer
(74) *Attorney, Agent, or Firm*—Milton L. Honig

(57) ABSTRACT

A personal care product is provided which includes a composition a quaternary ammonium salt wherein a cation of the salt is a dihydroxypropyltri($C_1$–$C_3$ alkyl)ammonium monosubstituted polyol in a carrier. The cation should have a molecular weight no higher than about 450 and the salt have a $T_g$ no higher than about 10° C. Particularly preferred are hydroxypropyltrimonium sorbitol salts. These salts operate as humectants to moisturize both in high and low relative humidity environments.

10 Claims, No Drawings

PERSONAL CARE COMPOSITION WITH SALTS OF DIHYDROXYPROPYLTRI($C_1$-$C_3$ ALKYL) AMMONIUM MONOSUBSTITUTED POLYOLS

BACKGROUND OF THE INVENTION

1. Field of the Invention

The invention concerns personal care compositions providing moisturization both in high and low relative humidity environments.

2. The Related Art

Dry skin is a problem in varying degree to most humans. This condition is particularly evident in winter. Personal care products such as skin creams/lotions, shampoos/conditioners, toilette bars/shower gels and antiperspirant/deodorants are normally formulated with at least one material to adress dry skin. Symptoms such as itching, flaking and a visually displeasing dermal appearance can all to some extend be modulated.

There are three classes of materials employed against the problem. Occlusives such as petrolatum or silicone oils serve to inhibit loss of natural moisture. They form a barrier between the epidermis and the environment. Another approach is the use of keratolytic agents to enhance rate of dermal exfoliation. Alpha-hydroxy acids are the most common agents for achieving exfoliation.

A third approach to dry skin is topical application of humectants. Hydroxylated monomeric and polymeric organic substances are generally used for this purpose. Glycerin known also as glycerol is one of the most effective humectants.

There are several shortcomings in the performance of known humectants. Even the best such as glycerin requires to be formulated at relatively high levels to achieve good moisturization. Secondly, known humectants perform well in high relative humidity environments; however, hardly any of these substances provide effectiveness at low relative humidity (i.e. less than 20% moisture at 20° C.). Average indoor relative humidity during winter is approximately 13% in areas such as the Northeast U.S. It is quite evident that a real need exists for an improved moisturization technology.

A moisturizer known as Honeyquat 50 with INCI name of Hydroxypropyltrimonium Honey has been reported to be a better humectant than glycerin. See the Arch/Brooks brochure titled "Cosmetic Ingredients & Ideas®", Issue No. 2, August 2001. Honeyquat 50 is described as being derived from the reaction of pendent hydroxyl groups (on the disaccharide) of a "light" deodorized grade of honey with a chlorohydroxytrimethylammonium derivative. Although this substance has excellent humectancy, moisturization at low relative humidity still remains to be conquered.

Accordingly, the present invention seeks to identify humectants which are operative not only at high but also low relative humidity, for application in personal care products.

SUMMARY OF THE INVENTION

A personal care composition which includes:
(i) from about 0.1 to about 30% by weight of a quaternary ammonium compound which is a salt of hydroxypropyltri($C_1$-$C_3$ alkyl) ammonium monosubstituted polyol, the cation having an average molecular weight no higher than about 450 and the salt having a $T_g$ no higher than about 10° C.; and
(ii) a cosmetically acceptable carrier.

DETAILED DESCRIPTION OF THE INVENTION

Now it has been found that salts wherein a cation is a hydroxypropyltri($C_1$-$C_3$ alkyl)ammonium monosubstituted polyol are excellent moisturizers providing humectancy in both high and low relative humidity environments. Amounts of these salts may range from about 0.1 to about 30%, preferably from about 0.5 to about 20%, optimally from about 1% to about 12% by weight of the composition.

Salts of hydroxypropyl tri($C_1$-$C_3$ alkyl) ammonium monosubstituted polyols can be formed in a variety of procedures. Most preferred is via reaction of 2-hydroxy-3-chloropropyl trimethyl ammonium chloride with a polyol, particularly a linear polyol in an approximately 1:1 molar ratio in an alkaline medium. By typical Williamson synthesis, sodium chloride is eliminated thereby forming an ether linkage between the hydroxypropyl end of the quat and the polyol. Typical polyols are sorbitol, pentaerythritol, neopentyl glycol, propylene glycol, dipropylene glycol and isoprene glycol.

The cation should have an average molecular weight no higher than about 450, preferably no higher than about 400, and optimally between about 300 and 400. Further, the salt advantageously is liquid at 23° C. Thus, the $T_g$ preferably is no higher than about 10° C., more preferably no higher than about 0° C. The $T_g$ can be measured in a Differential Scanning Calorimeter.

Ordinarily the $C_1$-$C_3$ alkyl constituent on the quaternized ammonium group will be methyl, ethyl, n-propyl, isopropyl or hydroxyethyl and mixtures thereof. Particularly preferred is a trimethyl ammonium group known through INCI nomenclature as a "trimonium" group. Any anion can be used in the quat salt. The anion may be organic or inorganic with proviso that the material is cosmetically acceptable. Typical inorganic anions are halides, sulfates, phosphates, nitrates and borates. Most preferred are the halides, especially chloride. Organic anionic counter ions include methosulfate, toluoyl sulfate, acetate, citrate, tartrate, lactate, gluconate, and benzenesulfonate.

Advantageously compositions of the present invention will be formulated with a quaternary ammonium salt where the polyol is only mono-substituted with hydroxypropyltri ($C_1$-$C_3$ alkyl) ammonium groups. However, smaller amounts of di- and tri-substituted polyol may also be present. These amounts normally may range from 0 to 20%, possibly from about 2 to about 10% by weight based on the weight of the quaternary ammonium compound present. More specifically, the multi-substituted polyol may be di-[hydroxypropyltri($C_1$-$C_3$ alkyl)ammonium] polyol, tri-[hydroxypropyltri($C_1$-$C_3$ alkyl) ammonium] polyol and mixtures thereof.

By the term personal care composition is meant any substance applied to a human body for improving appearance, cleansing, odor control or general aesthetics. Nonlimiting examples of personal care compositions include leave-on skin lotions and creams, shampoos, hair conditioners, shower gels, toilet bars, antiperspirants, deodorants, dental products, shave creams, depilatories, lipsticks, foundations, mascara, sunless tanners and sunscreen lotions.

Compositions of this invention will also include a cosmetically acceptable carrier. Amounts of the carrier may range from about 1 to about 99.9%, preferably from about 70 to about 95%, optimally from about 80 to about 90% by weight of the composition. Among the useful carriers are water, emollients, fatty acids, fatty alcohols, thickeners and combinations thereof. The carrier may be aqueous, anhydrous or an emulsion. Preferably the compositions are aqueous, especially water and oil emulsions of the W/O or O/W, or triplex W/O/W variety. Water when present may be in amounts ranging from about 5 to about 95%, preferably from about 20 to about 70%, optimally from about 35 to about 60% by weight.

Emollient materials may serve as cosmetically acceptable carriers. These may be in the form of silicone oils, natural or synthetic esters and hydrocarbons. Amounts of the emollients may range anywhere from about 0.1 to about 95%, preferably between about 1 and about 50% by weight of the composition.

Silicone oils may be divided into the volatile and nonvolatile variety. The term "volatile" as used herein refers to those materials which have a measurable vapor pressure at ambient temperature. Volatile silicone oils are preferably chosen from cyclic (cyclomethicone) or linear polydimethylsiloxanes containing from 3 to 9, preferably from 4 to 5, silicon atoms.

Nonvolatile silicone oils useful as an emollient material include polyalkyl siloxanes, polyalkylaryl siloxanes and polyether siloxane copolymers. The essentially nonvolatile polyalkyl siloxanes useful herein include, for example, polydimethyl siloxanes with viscosities of from about $5 \times 10^{-6}$ to $0.1$ m$^2$/s at 25° C. Among the preferred nonvolatile emollients useful in the present compositions are the polydimethyl siloxanes having viscosities from about $1 \times 10^{-5}$ to about $4 \times 10^{-4}$ m$^2$/s at 25° C.

Another class of nonvolatile silicones are emulsifying and non-emulsifying silicone elastomers. Representative of this category is Dimethicone/Vinyl Dimethicone Crosspolymer available as Dow Corning 9040, General Electric SFE 839, and Shin-Etsu KSG-18. Silicone waxes such as Silwax WS-L (Dimethicone Copolyol Laurate) may also be useful.

Among the ester emollients are:

a) Alkyl esters of saturated fatty acids having 10 to 24 carbon atoms. Examples thereof include behenyl neopentanoate, isononyl isonanonoate, isopropyl myristate and octyl stearate.

b) Ether-esters such as fatty acid esters of ethoxylated saturated fatty alcohols.

c) Polyhydric alcohol esters. Ethylene glycol mono and di-fatty acid esters, diethylene glycol mono- and di-fatty acid esters, polyethylene glycol (200–6000) mono- and di-fatty acid esters, propylene glycol mono- and di-fatty acid esters, polypropylene glycol 2000 monostearate, ethoxylated propylene glycol monostearate, glyceryl mono- and di-fatty acid esters, polyglycerol poly-fatty esters, ethoxylated glyceryl monostearate, 1,3-butylene glycol monostearate, 1,3-butylene glycol distearate, polyoxyethylene polyol fatty acid ester, sorbitan fatty acid esters, and polyoxyethylene sorbitan fatty acid esters are satisfactory polyhydric alcohol esters. Particularly useful are pentaerythritol, trimethylolpropane and neopentyl glycol esters of $C_1$–$C_{30}$ alcohols.

d) Wax esters such as beeswax, spermaceti wax and tribehenin wax.

e) Sugar ester of fatty acids such as sucrose polybehenate and sucrose polycottonseedate.

Natural ester emollients principally are based upon mono-, di- and tri-glycerides. Representative glycerides include sunflower seed oil, cottonseed oil, borage oil, borage seed oil, primrose oil, castor oil and hydrogenated castor oils, rice bran oil, soybean oil, olive oil, safflower oil, shea butter, jojoba oil and combinations thereof. Animal derived emollients are represented by lanolin oil and lanolin derivatives. Amounts of the natural esters may range from about 0.1 to about 20% by weight of the compositions.

Hydrocarbons which are suitable cosmetically acceptable carriers include petrolatum, mineral oil, $C_{11}$–$C_{13}$ isoparaffins, polybutenes, and especially isohexadecane, available commercially as Permethyl 101A from Presperse Inc.

Fatty acids having from 10 to 30 carbon atoms may also be suitable as cosmetically acceptable carriers. Illustrative of this category are pelargonic, lauric, myristic, palmitic, stearic, isostearic, oleic, linoleic, linolenic, hydroxystearic and behenic acids.

Fatty alcohols having from 10 to 30 carbon atoms are another useful category of cosmetically acceptable carrier. Illustrative of this category are stearyl alcohol, lauryl alcohol, myristyl alcohol, oleyl alcohol and cetyl alcohol.

Thickeners can be utilized as part of the cosmetically acceptable carrier of compositions according to the present invention. Typical thickeners include crosslinked acrylates (e.g. Carbopol 982®), hydrophobically-modified acrylates (e.g. Carbopol 1382®), polyacrylamides (e.g. Sepigel 305®), acryloylmethylpropane sulfonic acid/salt polymers and copolymers (e.g. Aristoflex HMB® and AVC®), cellulosic derivatives and natural gums. Among useful cellulosic derivatives are sodium carboxymethylcellulose, hydroxypropyl methocellulose, hydroxypropyl cellulose, hydroxyethyl cellulose, ethyl cellulose and hydroxymethyl cellulose. Natural gums suitable for the present invention include guar, xanthan, sclerotium, carrageenan, pectin and combinations of these gums. Inorganics may also be utilized as thickeners, particularly clays such as bentonites and hectorites, fumed silicas, talc, calcium carbonate and silicates such as magnesium aluminum silicate (Veegum®). Amounts of the thickener may range from 0.0001 to 10%, usually from 0.001 to 1%, optimally from 0.01 to 0.5% by weight of the composition.

Adjunct humectants may be employed in the present invention. These are generally polyhydric alcohol-type materials. Typical polyhydric alcohols include glycerol, propylene glycol, dipropylene glycol, polypropylene glycol, polyethylene glycol, sorbitol, hydroxypropyl sorbitol, hexylene glycol, 1,3-butylene glycol, isoprene glycol, 1,2,6-hexanetriol, ethoxylated glycerol, propoxylated glycerol and mixtures thereof. The amount of adjunct humectant may range anywhere from 0.5 to 50%, preferably between 1 and 15% by weight of the composition.

Personal care compositions of the present invention may be in any form. These forms may include lotions, creams, roll-on formulations, sticks, mousses, aerosol and non-aerosol sprays and fabric (e.g. nonwoven textile)-applied formulations.

Surfactants may also be present in compositions of the present invention. Total concentration of the surfactant when present may range from about 0.1 to about 90%, preferably from about 1 to about 40%, optimally from about 1 to about 20% by weight of the composition, and being highly dependent upon the type of personal care product. The surfactant may be selected from the group consisting of anionic, nonionic, cationic and amphoteric actives. Particularly preferred nonionic surfactants are those with a $C_{10}$–$C_{20}$ fatty alcohol or acid hydrophobe condensed with from 2 to 100 moles of ethylene oxide or propylene oxide per mole of hydrophobe; $C_2$–$C_{10}$ alkyl phenols condensed with from 2 to 20 moles of alkylene oxide; mono- and di-fatty acid esters of ethylene glycol; fatty acid monoglyceride; sorbitan, mono- and di- $C_8$–$C_{20}$ fatty acids; and polyoxyethylene sorbitan as well as combinations thereof. Alkyl polyglycosides and saccharide fatty amides (e.g. methyl gluconamides) and trialkylamine oxides are also suitable nonionic surfactants.

Preferred anionic surfactants include soap, alkyl ether sulfates and sulfonates, alkyl sulfates and sulfonates, alkylbenzene sulfonates, alkyl and dialkyl sulfosuccinates, $C_8-C_{20}$ acyl isethionates, $C_8-C_{20}$ alkyl ether phosphates, $C_8-C_{20}$ sarcosinates, $C_8-C_{20}$ acyl lactylates, sulfoacetates and combinations thereof.

Useful amphoteric surfactants include cocoamidopropyl betaine, $C_{12}-C_{20}$ trialkyl betaines, sodium lauroamphoacetate, and sodium laurodiamphoacetate.

Sunscreen agents may also be included in compositions of the present invention. Particularly preferred are such materials as ethylhexyl p-methoxycinnamate, available as Parsol MCX®, Avobenzene, available as Parsol 1789® and benzophenone-3, also known as Oxybenzone. Inorganic sunscreen actives may be employed such as microfine titanium dioxide and zinc oxide. Amounts of the sunscreen agents when present may generally range from 0.1 to 30%, preferably from 2 to 20%, optimally from 4 to 10% by weight of the composition.

Antiperspirants and deodorant compositions of the present invention ordinarily will contain astringent actives. Examples include aluminum chloride, aluminum chlorhydrex, aluminum-zirconium chlorhydrex glycine, aluminum sulfate, zinc sulfate, zirconium and aluminum chlorohydroglycinate, zirconium hydroxychloride, zirconium and aluminum lactate, zinc phenolsulfonate and combinations thereof. Amounts of the astringents may range anywhere from about 0.5 to about 50% by weight of the composition.

Dental products formulated according to the present invention will generally contain a fluoride source to prevent dental caries. Typical anti-caries actives include sodium fluoride, stannous fluoride and sodium monofluoro phosphate. Amounts of these materials will be determined by the amount of fluoride releasable which should range between about 500 to about 8800 ppm of the composition. Other components of dentifrices can include desensitizing agents such as potassium nitrate and strontium nitrate, sweeteners such as sodium saccharine, aspartame, sucralose, and potassium acesulfam. Thickeners, opacifying agents, abrasives and colorants will normally also be present.

Preservatives can desirably be incorporated into the personal care compositions of this invention to protect against the growth of potentially harmful microorganisms. Particularly preferred preservatives are phenoxyethanol, methyl paraben, propyl paraben, imidazolidinyl urea, dimethyloldimethylhydantoin, ethylenediaminetetraacetic acid salts (EDTA), sodium dehydroacetate, methylchloroisothiazolinone, methylisothiazolinone, iodopropynbutylcarbamate and benzyl alcohol. The preservatives should be selected having regard for the use of the composition and possible incompatibilities between the preservatives and other ingredients. Preservatives are preferably employed in amounts ranging from 0.01% to 2% by weight of the composition.

Compositions of the present invention may include vitamins. Illustrative vitamins are Vitamin A (retinol), Vitamin $B_2$, Vitamin $B_3$ (niacinamide), Vitamin $B_6$, Vitamin C, Vitamin E, Folic Acid and Biotin. Derivatives of the vitamins may also be employed. For instance, Vitamin C derivatives include ascorbyl tetraisopalmitate, magnesium ascorbyl phosphate and ascorbyl glycoside. Derivatives of Vitamin E include tocopheryl acetate, tocopheryl palmitate and tocopheryl linoleate. DL-panthenol and derivatives may also be employed. For purposes of this invention, vitamins where present are not considered as unsaturated materials. Total amount of vitamins when present in compositions according to the present invention may range from 0.001 to 10%, preferably from 0.01% to 1%, optimally from 0.1 to 0.5% by weight of the composition.

Another type of useful substance can be that of an enzyme such as amylases, oxidases, proteases, lipases and combinations. Particularly preferred is superoxide dismutase, commercially available as Biocell SOD from the Brooks Company, USA.

Skin lightening compounds may be included in the compositions of the invention. Illustrative substances are placental extract, lactic acid, niacinamide, arbutin, kojic acid, ferulic acid, resorcinol and derivatives including 4-substituted resorcinols and combinations thereof. Amounts of these agents may range from about 0.1 to about 10%, preferably from about 0.5 to about 2% by weight of the composition.

Desquamation promoters may be present. Illustrative are the alpha-hydroxycarboxylic acids and beta-hydroxycarboxylic acids. The term "acid" is meant to include not only the free acid but also salts and $C_1-C_{30}$ alkyl or aryl esters thereof and lactones generated from removal of water to form cyclic or linear lactone structures. Representative acids are glycolic, lactic and malic acids. Salicylic acid is representative of the beta-hydroxycarboxylic acids. Amounts of these materials when present may range from about 0.01 to about 15% by weight of the composition.

A variety of herbal extracts may optionally be included in compositions of this invention. The extracts may either be water soluble or water-insoluble carried in a solvent which respectively is hydrophilic or hydrophobic. Water and ethanol are the preferred extract solvents. Illustrative extracts include those from green tea, chamomile, licorice, aloe vera, grape seed, citrus unshui, willow bark, sage, thyme and rosemary.

Also included may be such materials as lipoic acid, retinoxytrimethylsilane (available from Clariant Corp. under the Silcare 1M-75 trademark), dehydroepiandrosterone (DHEA) and combinations thereof. Ceramides (including Ceramide 1, Ceramide 3, Ceramide 3B and Ceramide 6) as well as pseudoceramides may also be useful. Amounts of these materials may range from about 0.000001 to about 10%, preferably from about 0.0001 to about 1% by weight of the composition.

Colorants, opacifiers and abrasives may also be included in compositions of the present invention. Each of these substances may range from about 0.05 to about 5%, preferably between 0.1 and 3% by weight of the composition.

The compositions of the present invention can also be, optionally, incorporated into an insoluble substrate for application to the skin such as in the form of a treated wipe.

A wide variety of packaging can be employed to store and deliver the personal care compositions. Packaging is often dependent upon the type of personal care end-use. For instance, leave-on skin lotions and creams, shampoos, conditioners and shower gels generally employ plastic containers with an opening at a dispensing end covered by a closure. Typical closures are screw-caps, non-aerosol pumps and flip-top hinged lids. Packaging for antiperspirants, deodorants and depilatories may involve a container with a roll-on ball on a dispensing end. Alternatively these types of personal care products may be delivered in a stick composition formulation in a container with propel-repel mechanism where the stick moves on a platform towards a dispensing orifice. Metallic cans pressurized by a propellant and having a spray nozzle serve as packaging for antiperspirants, shave creams and other personal care products. Toilette bars may have packaging constituted by a cellulosic or plastic wrapper or within a cardboard box or even encompassed by a shrink wrap plastic film. All of the aforementioned are considered packaging within context of the present invention.

The term "comprising" is meant not to be limiting to any subsequently stated elements but rather to encompass non-specified elements of major or minor functional importance. In other words the listed steps, elements or options need not be exhaustive. Whenever the words "including" or "having" are used, these terms are meant to be equivalent to "comprising" as defined above.

Except in the operating and comparative examples, or where otherwise explicitly indicated, all numbers in this description indicating amounts of material ought to be understood as modified by the word "about".

All documents referred to herein, including all patents, patent applications, and printed publications, are hereby incorporated by reference in their entirety in this disclosure.

The following examples will more fully illustrate the embodiments of this invention. All parts, percentages and proportions referred to herein and in the appended claims are by weight unless otherwise illustrated.

EXAMPLE 1

A representative personal care composition of the present invention in the form of a cosmetic lotion is outlined under Table 1.

TABLE I

| INGREDIENT | WEIGHT % |
|---|---|
| PHASE A | |
| Water | Balance |
| Disodium EDTA | 0.05 |
| Methyl Paraben | 0.15 |
| Magnesium Aluminum Silicate | 0.60 |
| Triethanolamine | 1.20 |
| Chloride Salt of Hydroxypropyltrimonium Sorbitol | 1.00 |
| PHASE B | |
| Xanthan Gum | 0.20 |
| Natrosol ® 250HHR (ethyl cellulose) | 0.50 |
| Butylene Glycol | 3.00 |
| Glycerin | 2.00 |
| PHASE C | |
| Sodium Stearoyl Lactylate | 0.10 |
| Glycerol Monostearate | 1.50 |
| Stearyl Alcohol | 1.50 |
| Isostearyl Palmitate | 3.00 |
| Silicone Fluid | 1.00 |
| Cholesterol | 0.25 |
| Sorbitan Stearate | 1.00 |
| Butylated Hydroxy Toluene | 0.05 |
| Vitamin E Acetate | 0.01 |
| PEG-100 Stearate | 2.00 |
| Stearic Acid | 3.00 |
| Propyl Paraben | 0.10 |
| Parsol MCX ® | 2.00 |
| Caprylic/Capric Triglyceride | 0.50 |
| Hydroxycaprylic Acid | 0.01 |
| C12–15 Alkyl Octanoate | 3.00 |
| PHASE D | |
| Vitamin A Palmitate | 0.10 |
| Bisabolol | 0.01 |
| Vitamin A Acetate | 0.01 |
| Fragrance | 0.03 |
| Retinol 50C | 0.02 |
| Conjugated Linoleic Acid | 0.50 |

EXAMPLE 2

A water-in-oil topical liquid make-up foundation according to invention is described in Table II below.

TABLE II

| INGREDIENT | WEIGHT % |
|---|---|
| PHASE A | |
| Cyclomethicone | 9.25 |
| Oleyl Oleate | 2.00 |
| Dimethicone Copolyol | 20.00 |
| PHASE B | |
| Talc | 3.38 |
| Pigment (Iron Oxides) | 10.51 |
| Spheron L-1500 (Silica) | 0.50 |
| PHASE C | |
| Synthetic Wax Durachem 0602 | 0.10 |
| Arachidyl Behenate | 0.30 |
| PHASE D | |
| Cyclomethicone | 1.00 |
| Trihydroxystearin | 0.30 |
| PHASE E | |
| Laureth-7 | 0.50 |
| Propyl Paraben | 0.25 |
| PHASE F | |
| Fragrance | 0.05 |
| PHASE G | |
| Water | balance |
| Chloride Salt of Hydroxypropyltrimonium Sorbitol | 3.00 |
| Methyl Paraben | 0.12 |
| Propylene Glycol | 8.00 |
| Niacinamide | 4.00 |
| Glycerin | 3.00 |
| Sodium Chloride | 2.00 |
| Sodium Dehydroacetate | 0.30 |

EXAMPLE 3

Illustrated herein is a skin cream incorporating a quat salt of the present invention.

TABLE III

| INGREDIENT | WEIGHT % |
|---|---|
| Glycerin | 6.93 |
| Niacinamide | 5.00 |
| Chloride Salt of Hydroxypropyltrimonium Sorbitol | 5.00 |
| Permethyl 101A[1] | 3.00 |
| Sepigel 305[2] | 2.50 |
| Q2-1403[3] | 2.00 |
| Linseed Oil | 1.33 |
| Arlatone 2121[4] | 1.00 |
| Cetyl Alcohol CO-1695 | 0.72 |
| SEFA Cottonate[5] | 0.67 |
| Tocopherol Acetate | 0.50 |
| Panthenol | 0.50 |
| Stearyl Alcohol | 0.48 |
| Titanium Dioxide | 0.40 |

TABLE III-continued

| INGREDIENT | WEIGHT % |
| --- | --- |
| Disodium EDTA | 0.10 |
| Glydant Plus[6] | 0.10 |
| PEG-100 Stearate | 0.10 |
| Stearic Acid | 0.10 |
| Purified Water | Balance |

[1]Isohexadecane, Presperse Inc., South Plainfield, NJ
[2]Polyacrylamide (and) C13–14 Isoparaffin (and) Laureth-7, Seppic Corporation, Fairfield, NJ
[3]dimethicone (and) dimethiconol, Dow Corning Corp. Midland, MI
[4]Sorbitan Monostearate and Sucrococoate, ICI Americas Inc., Wilmington, DE
[5]Sucrose ester of fatty acid
[6]DMDM Hydantoin (and) Iodopropynyl Butylcarbamate, Lonza Inc., Fairlawn, NJ

EXAMPLE 4

Illustrative of another cosmetic composition incorporating a quat salt according to the present invention is the formula of Table IV.

TABLE IV

| INGREDIENT | WEIGHT % |
| --- | --- |
| Polysilicone-11 | 29 |
| Cyclomethicone | 59 |
| Petrolatum | 11 |
| Chloride Salt of Hydroxypropyltrimonium Sorbitol | 0.2 |
| Dimethicone Copolyol | 0.3 |
| Sunflowerseed Oil | 0.5 |

EXAMPLE 5

A relatively anhydrous composition incorporating a quat salt of the present invention is reported in Table V.

TABLE V

| INGREDIENT | WEIGHT % |
| --- | --- |
| Cyclomethicone | 80.65 |
| Dimethicone | 9.60 |
| Squalane | 6.00 |
| Isostearic Acid | 1.90 |
| Borage Seed Oil | 0.90 |
| Chloride Salt of Hydroxypropyltrimonium Sorbitol | 0.50 |
| Retinyl Palmitate | 0.25 |
| Ceramide 6 | 0.10 |
| Tocopherol | 0.10 |

EXAMPLE 6

An aerosol packaged foaming cleanser with a quat salt suitable for the present invention is outlined in Table VI.

TABLE VI

| INGREDIENT | WEIGHT % |
| --- | --- |
| Sunflower Seed Oil | 20.00 |
| Maleated Soybean Oil | 5.00 |
| Silicone Urethane | 1.00 |
| Polyglycero-4 Oleate | 1.00 |
| Sodium C14–16 Olefin Sulfonate | 15.00 |
| Sodium Lauryl Ether Sulphate (25% active) | 15.00 |
| Cocoamidopropylbetaine | 15.00 |

TABLE VI-continued

| INGREDIENT | WEIGHT % |
| --- | --- |
| DC 1784 ® (Silicone Emulsion 50%) | 5.00 |
| Polyquaternium-11 | 1.00 |
| Chloride Salt of Hydroxypropyltrimonium Sorbitol | 1.00 |
| Water | Balance |

EXAMPLE 7

A disposable, single use personal care towelette product is described according to the present invention. A 70/30 polyester/rayon non-woven towelette is prepared with a weight of 1.8 grams and dimensions of 15 cm by 20 cm. Onto this towelette is impregnated a composition with a quaternary ammonium salt as outlined in Table VII below.

TABLE VII

| INGREDIENT | WEIGHT % |
| --- | --- |
| Chloride Salt of Hydroxypropyltrimonium Sorbitol | 7.50 |
| Glycerin | 2.00 |
| Hexylene Glycol | 2.00 |
| Disodium Capryl Amphodiacetate | 1.00 |
| Gluconolactone | 0.90 |
| Silicone Microemulsion | 0.85 |
| Witch Hazel | 0.50 |
| PEG-40 Hydrogenated Castor Oil | 0.50 |
| Fragrance (Terpenoid Mixture) | 0.20 |
| Vitamin E Acetate | 0.001 |
| Water | Balance |

EXAMPLE 8

A toilette bar illustrative of the present invention is outlined under Table VIII.

TABLE VIII

| INGREDIENT | WEIGHT % |
| --- | --- |
| Sodium Soap (85/15 Tallow/Coconut) | 77.77 |
| Chloride Salt of Hydroxypropyltrimonium Sorbitol | 3.50 |
| Glycerin | 2.50 |
| Sodium Chloride | 0.77 |
| Titanium Dioxide | 0.40 |
| Fragrance | 1.50 |
| Disodium EDTA | 0.02 |
| Sodium Etidronate | 0.02 |
| Fluorescer | 0.024 |
| Water | Balance |

EXAMPLE 9

A shampoo composition useful in the context of the present invention is described in Table IX below.

TABLE IX

| Ingredient | Weight % |
| --- | --- |
| Ammonium Laureth Sulfate | 12.00 |
| Ammonium Lauryl Sulfate | 2.00 |
| Cocoamidopropyl Betaine | 2.00 |
| Sodium Lauroamphoacetate | 2.00 |
| Chloride Salt of Hydroxypropyltrimonium Neopentyl Glycol | 5.50 |
| Ethylene Glycol Distearate | 1.50 |

TABLE IX-continued

| Ingredient | Weight % |
| --- | --- |
| Cocomonoethanolamide | 0.80 |
| Cetyl Alcohol | 0.60 |
| Polyquaternium-10 | 0.50 |
| Dimethicone | 1.00 |
| Zinc Pyridinethione | 1.00 |
| Sodium Citrate | 0.40 |
| Citric Acid | 0.39 |
| Sodium Xylene Sulfonate | 1.00 |
| Fragrance | 0.40 |
| Sodium Benzoate | 0.25 |
| Kathon CG ® | 0.0008 |
| Benzyl Alcohol | 0.0225 |
| Water | Balance |

EXAMPLE 10

This Example illustrates an antiperspirant/deodorant formula incorporating the moisturizing actives according to the present invention.

TABLE X

| Ingredient | Weight % |
| --- | --- |
| Cyclopentacycloxane | 44 |
| Dimethicone | 20 |
| Aluminum Zirconium Trichlorohydrex Glycinate | 15 |
| Chloride Salt of Hydroxpropyltrimonium Isoprene Glycol | 5.0 |
| $C_{18}$–$C_{36}$ Acid Triglyceride | 5.0 |
| Microcrystalline Wax | 3.0 |
| Glycerin | 3.0 |
| Silica | 2.5 |
| Dimethicone Crosspolymer | 1.0 |
| Fragrance | 0.5 |
| Disodium EDTA | 0.4 |
| Butylated Hydroxytoluene | 0.3 |
| Citric Acid | 0.3 |

EXAMPLE 11

A toothpaste according to the present invention can be formulated with the ingredients listed under Table XI.

TABLE XI

| Ingredients | Weight % |
| --- | --- |
| Zeodent 115 ® | 20.00 |
| Glycerin | 18.00 |
| Xanthan Gum | 7.00 |
| Sodium Carboxymethyl Cellulose | 0.50 |
| Sodium Bicarbonate | 2.50 |
| Acetate Salt of Hydroxypropyltrimonium Sorbitol | 2.00 |
| Sodium Laurylsulfate | 1.50 |
| Sodium Fluoride | 1.10 |
| Sodium Saccharin | 0.40 |
| Titanium Dioxide | 1.00 |
| Pluronic F-127 ® | 2.00 |
| FD&C Blue No. 1 | 3.30 |
| Menthol | 0.80 |
| Potassium Nitrate | 5.00 |
| Water | balance |

EXAMPLE 12

This Example provides the results of moisturization efficacy tests. These tests involved evaluation on Porcine epidermis utilized as a human skin model. Equipment and protocol are outlined below.

An environmental microbalance (Model MB-300W, VTI Corp., 2708 W 84$^{th}$ Street, Hialeah, Fla. 33016) was programmed to measure the change in weight of porcine skin as a function of relative humidity at a constant temperature and airflow. The porcine skin was evaluated before and after treatment with aqueous solutions of humectants to determine adsorption and retention of moisture.

Sample preparation was done as follows:

Epidermal sections of porcine skin were cut to approximately 4 cm×1 cm.

The skin was washed in a 10% detergent solution and dried in a dessicator to a constant weight. This represents the Untreated material.

The skin was soaked in a 1% by weight aqueous solution of the test sample for 15 minutes, excess fluid was blotted off and the skin was dried to constant weight in a dessicator. This represents the Treated material.

Sequence of conditions for the microbalance was as follows:

30 minutes at 0% relative humidity. (Insures that sample is dry.)

90 minutes at 80% relative humidity. (Determines amount of water picked up.)

90 minutes at 20% relative humidity. (Determines amount of water retained.)

The experiments were conducted as follows:

The weight of a piece of untreated skin was recorded continuously during the sequence.

The piece of untreated skin was treated with the test sample.

The weight of the treated piece of skin was recorded continuously during the sequence.

Data reduction consisted of calculating the percent weight change from the initial weight for the untreated and treated pieces of skin.

The reported data was the difference between each treated piece and its corresponding untreated piece. Results are recorded in Table XII.

TABLE XII

| Sample* | From 0 through 80% Relative Humidity | From 0 to 80 to 20% Relative Humidity |
| --- | --- | --- |
| Sorbitol Monoquat | 1.98 | 3.00 |
| Honeyquat ® | 0.31 | 0.70 |
| Honey | 0.24 | 0.02 |
| Quat ® 188 | 0.21 | 0.10 |
| Glycerin | 0.21 | 0.10 |

*All samples tested at 1% active material in water solution.
Data points represent the difference in weight of treated skin minus untreated skin.

Evident from the results is that the monoquaternized sorbitol was not only effective for moisturizing at relatively high humidity but also exceptional at relatively low humidity. These results were especially significant relative to glycerin which is normally used for moisturization purposes in cosmetic formulations.

EXAMPLE 13

Herein is provided a synthesis procedure for the chloride salt of hydroxypropyltrimonium sorbitol (also referred to as 'Sorbitol Monoquat'). A round bottom 250 ml flask was fitted with a mechanical stirrer. Into the flask was charged a mixture of sorbitol (10 g, 55.0 mmol) and 3-chloro-2-hydroxypropyl trimethylammonium chloride (Quat 188®) (15 ml, 55.0 mmol). One molar sodium hydroxide (55.0 ml, 55.0 mmol) was then added to the charged mixture. The resultant solution was stirred at room temperature for 18 hours. Water was then removed under reduced pressure at 50° C. yielding a heterogeneous colorless syrup. Filtration through glass wool afforded sorbitol hydroxypropyltrimethylammonium chloride as a homogeneous clear syrup: m/z (ESI; $M^+$-$Cl^-$) 298.

What is claimed is:

1. A personal care composition comprising:
   (i) from about 0.1 to about 30% by weight of a quaternary ammonium salt wherein a cation of the salt is a hydroxypropyltri($C_1$–$C_3$ alkyl) ammonium monosubstituted polyol, the cation having an average molecular weight no higher than about 450 and the salt having a $T_g$ no higher than about 10° C.; and
   (ii) a cosmetically acceptable carrier.

2. The composition according to claim 1 wherein the average molecular weight is no higher than about 400.

3. The composition according to claim 1 wherein the quaternary ammonium salt is present in an amount from about 1.5 to about 12% by weight of the composition.

4. The composition according to claim 1 which is selected from the group consisting of leave-on skin lotions and creams, shampoos, hair conditioners, shower gels, toilette bars, antiperspirants, deodorants, dental products, shave creams, depilatories, lipsticks, foundations, mascara, sunless tanner and sunscreen lotions.

5. The composition according to claim 1 wherein the polyol is selected from the group consisting of sorbitol, pentaerythritol, neopentyl glycol, propylene glycol, dipropylene glycol and isoprene glycol.

6. The composition according to claim 1 wherein the quaternary ammonium salt is a chloride of hydroxypropyl trimonium sorbitol.

7. A method for moisturizing skin comprising applying to the skin a composition comprising:
   (i) from about 0.1 to about 30% by weight of a quaternary ammonium salt wherein a cation of the salt is a hydroxypropyltri($C_1$–$C_3$ alkyl) ammonium monosubstituted polyol, the cation having an average molecular weight no higher than about 450 and the salt having a $T_g$ no higher than about 10° C.; and
   (ii) a cosmetically acceptable carrier.

8. The method according to claim 7 wherein the quaternary ammonium salt is a chloride of hydroxypropyl trimonium sorbitol.

9. The method according to claim 7 wherein the average molecular weight is no higher than about 400.

10. The method according to claim 7 wherein the polyol is selected from the group consisting of sorbitol, pentaerythritol, neopentyl glycol, propylene glycol, dipropylene glycol and isoprene glycol.

* * * * *